United States Patent [19]
Cauffriez et al.

[11] Patent Number: 6,121,186
[45] Date of Patent: *Sep. 19, 2000

[54] CATALYST BASED ON A HALOGENATED ALUMINA, ITS PREPARATION AND USE FOR THE ISOMERIZATION OF NORMAL $C_4$-$C_6$ PARAFFINS

[75] Inventors: Hervé Cauffriez, Bougival; Christine Travers, Rueil Malmaison, both of France

[73] Assignee: Institut Francais du Petrole, Rueil-Malmaison, France

[ * ] Notice: This patent is subject to a terminal disclaimer.

[21] Appl. No.: 08/962,618

[22] Filed: Nov. 3, 1997

Related U.S. Application Data

[63] Continuation-in-part of application No. 08/671,340, Jun. 27, 1996, abandoned.

[30] Foreign Application Priority Data

Jun. 28, 1995 [FR] France ................................... 95 07887

[51] Int. Cl.[7] .......................... B01J 27/13; B01J 27/125; B01J 23/42; C07C 5/13
[52] U.S. Cl. .......................... 502/230; 502/231; 502/327; 502/332; 502/334; 502/339; 585/748; 585/749
[58] Field of Search ..................................... 502/229, 230, 502/231, 327, 332, 333, 334, 335, 336, 339; 585/748, 749

[56] References Cited

U.S. PATENT DOCUMENTS

| | | | |
|---|---|---|---|
| 3,242,228 | 3/1966 | Riordan et al. | 260/683.68 |
| 3,449,264 | 6/1969 | Meyers | 252/441 |
| 3,553,281 | 1/1971 | Gobel et al. | 260/683.68 |
| 3,963,643 | 6/1976 | Germanas et al. | 252/442 |
| 4,003,849 | 1/1977 | Nelson | 252/442 |
| 4,018,839 | 4/1977 | Rausch | 260/666 R |
| 4,039,604 | 8/1977 | Myers et al. | 260/683.68 |
| 4,085,157 | 4/1978 | Juguin et al. | 260/673 |
| 4,333,856 | 6/1982 | Antos | 252/441 |
| 5,182,248 | 1/1993 | Cody et al. | 502/230 |
| 5,607,891 | 3/1997 | Travers et al. | 502/229 |

FOREIGN PATENT DOCUMENTS

91/17825  11/1991  WIPO .

*Primary Examiner*—Walter D. Griffin
*Assistant Examiner*—Thuan D. Dang
*Attorney, Agent, or Firm*—Millen, White, Zelano & Branigan, P.C.

[57] ABSTRACT

The invention concerns a catalyst composed of at least one halogen, at least one metal from group VIII and a formed support of gamma alumina and optionally eta alumina, the catalyst being characterized in that the smallest average dimension of said support is in the range 0.8 mm to 2 mm and in that the halogen content is in the range 4.5% to 15% by weight. The invention also concerns the preparation of said catalyst, preferably with chlorination (in the case where the halogen is chlorine) in the presence of $CCl_4$ or $CHCl_3$. The invention also concerns the use of the catalyst for the isomerisation of normal $C_4$–$C_6$ paraffins.

12 Claims, No Drawings

CATALYST BASED ON A HALOGENATED ALUMINA, ITS PREPARATION AND USE FOR THE ISOMERIZATION OF NORMAL $C_4$-$C_6$ PARAFFINS

CROSS-REFERENCE TO RELATED APPLICATION

This application is a continuation-in-part of application Ser. No. 08/671,340, now abandoned filed Jun. 27, 1996.

BACKGROUND OF THE INVENTION

The present invention concerns a catalyst based on a halogenated alumina, preferably chlorinated, its preparation and use in a process for the isomerisation of normal $C_4$–$C_6$ paraffins.

Isomerisation of normal paraffins containing 4 to 6 carbon atoms per molecule has now assumed considerable importance in the petroleum industry, mainly because of the removal of lead alkyls from petrol.

Isomerisation of n-butane produces isobutane for the aliphatic alkylation of olefins and for the synthesis of MTBE (methyl tertiobutyl ether) by dehydrogenating isobutane, to produce an alkylate with a high octane number and MTBE respectively, which compounds can be incorporated into petrol fractions.

Isomerisation of normal $C_5$–$C_6$ paraffins can transform paraffins with low octane numbers to isoparaffins with high octane numbers.

Three types of catalyst are traditionally used to carry out the isomerisation of normal paraffins containing 4 to 6 carbon atoms per molecule, preferably 5 to 6 carbon atoms per molecule:

Friedel-Crafts type catalysts, such as aluminium chloride, which are used at low temperatures (about 80° C. to 130° C.);

catalysts comprising at least one metal from group VIII on a support based on a halogenated, preferably chlorinated, alumina, used at medium temperatures (about 150° C.);

zeolitic catalysts comprising at least one metal from group VIII deposited on a zeolite, used at high temperatures (250° C. and more); those catalysts lead to smaller gains in the octane number of the products obtained than with the two catalyst types described above but have the advantage of being easier to use and more resistant to poisons. Nevertheless, they cannot be used to isomerise n-butane since they also produce a lower acidity than the two types of catalyst described above.

A number of patents concern monometallic catalysts based on platinum deposited on a halogenated alumina and their use in isomerisation processes of normal paraffins. An example is U.S. Pat. No. 3,963,643 which involves treatment with a Friedel-Crafts type compound followed by treatment with a chlorinated compound containing at least two chlorine atoms.

More recently, U.S. Pat No. 5,166,121 has claimed a catalyst comprising gamma alumina formed into spherules and containing between 0.1% and 3.5% of halogen on the support. An extremely small amount of halogen, preferably chlorine, is deposited on the support.

SUMMARY OF THE INVENTION

The invention concerns a catalyst containing at least one halogen, at least one metal from group VIII and a formed support comprising gamma alumina and optionally eta alumina, the catalyst being characterized in that the smallest average dimension of said support is in the range 0.8 mm to 2 mm, preferably in the range 1 mm to 1.8 mm, and in that the chlorine content is in the range 4.5% to 15% by weight, preferably in the range 5% to 12% by weight.

The support for the catalyst of the invention is alumina based, i.e., it essentially comprises alumina. The alumina support is gamma alumina to which eta alumina may optionally be added. When eta alumina is added to the gamma alumina, the alumina in the support generally comprises between 50% and 100% (limits excluded), preferably between 80% and 100% (limits excluded) (% by weight) of eta alumina, the complement being gamma alumina.

The smallest average dimension of the support of the catalyst of the invention is in the range 0.8 mm to 2 mm, preferably in the range 1 mm to 1.8 mm. Preferably, the support is essentially formed of spherules with an average diameter in the range 0.8 mm to 2 mm, preferably in the range 1 mm to 1.8 mm, or the support is essentially formed of extrudates whose smallest dimension is in the range 0.8 mm to 2 mm, preferably in the range 1 mm to 1.8 mm, i.e., the extrudates are formed using any extrusion technique which is known to the skilled person, for example a die with a diameter in the range 0.8 mm to 2 mm, preferably in the range 1 mm to 1.8 mm.

The gamma alumina present in the support of the catalyst of the invention has a specific surface area which is generally in the range 150 $m^2$/g to 300 $m^2$/g, preferably in the range 180 $m^2$/g to 250 $m^2$/g, and a total pore volume which is generally in the range 0.4 $cm^3$/g to 0.8 $cm^3$/g, preferably in the range 0.45 $cm^3$/g to 0.7 $cm^3$/g.

The eta alumina which may optionally be present in the support of the catalyst of the invention has a specific surface area which is generally in the range 400 $m^2$/g to 600 $m^2$/g, preferably in the range 420 $m^2$/g to 550 $m^2$/g, and a total pore volume which is generally in the range 0.3 $cm^3$/g to 0.5 $cm^3$/g, preferably in the range 0.35 $cm^3$/g to 0.45 $cm^3$/g.

The metal from group VIII is selected from the group formed by iron, cobalt, nickel, ruthenium, rhodium, palladium, osmium, iridium and platinum, preferably selected from the group formed by platinum, palladium and nickel. In the preferred case where the metal is platinum or palladium, the content is in the range 0.05% to 1% by weight, preferably in the range 0.1% to 0.6% by weight. In the preferred case where the metal is nickel, the content is in the range 0.1% to 10% by weight, preferably in the range 0.2% to 5%.

The catalyst of the invention comprises at least one halogen, in an amount in the range 4.5% to 15% by weight, preferably in the range 5% to 12% by weight. The halogen is selected from the group formed by fluorine, chlorine, bromine and iodine. Preferably, the halogen is chlorine.

The catalyst of the invention is generally prepared by forming a support then depositing at least one metal from group VIII on the formed support, and finally halogenation, preferably chlorination, after an optional preferred step of activation in hydrogen. Each step in the process for preparing the support of the invention is described below.

When eta alumina is present in the support of the catalyst of the invention, the two types of alumina are preferably mixed and used together, using any technique which is known to the skilled person, for example by extrusion through a die, pelletization or bowl granulation. It is also possible to form the two types of alumina separately then mix the two formed types of alumina. In all cases, the smallest dimension of the geometric shape adopted by the support after forming is in the range 0.8 mm to 2 mm, preferably in the range 1 mm to 1.8 mm, so that, during the support chlorination step, a sufficient chlorine content is obtained for a reduced chlorination period.

At least one hydrogenating metal from group VIII, preferably selected from the group formed by platinum, palladium and nickel, is then deposited on the support using any technique which is known to the skilled person, for example anion exchange in the form of hexachloroplatinic acid in the case of platinum or in the form of the chloride in the case of palladium.

Once the metal(s) has/have been deposited, the catalyst may undergo activation in air at high temperature, for example at a temperature in the range 300° C. to 700° C., then treatment in hydrogen to obtain an active metallic phase. This hydrogen treatment procedure can, for example, comprise a slow rise of temperature in a hydrogen stream up to the maximum reduction temperature, generally between about 300° C. and 700° C., preferably between about 340° C. and 680° C., followed by holding that temperature, generally for 1 to 6 hours, preferably for 1.5 to 4.5 hours.

The halogen, preferably chlorine, is deposited from any known compound to effect halogenation, preferably chlorination, under suitable conditions (as regards the treatment of effluents, halogenation period, cost . . . ). Thus the use of hydrogen chloride is excluded from the scope of the invention (see examples). Halogenation, preferably chlorination, of the alumina is effected remote from or directly in the reaction unit in which the catalyst is used, preferably in an isomerisation unit, using any halogenating agent, preferably a chlorinating agent, which is known to the skilled person. Preferably, when the halogen is chlorine, carbon tetrachloride or chloroform is used, as will be exemplified below.

The halogenation treatment, preferably chlorination treatment, can be carried out directly in the unit in which the catalyst of the invention is used, before injection of the feed, or it can be carried out offsite.

The use of a support characterized in that its smallest average dimension is in the range 0.8 mm to 2 mm, preferably in the range 1 mm to 1.8 mm, and in that the halogen content, preferably the chlorine content, is in the range 4.5% to 15% by weight, preferably in the range 5% to 12% by weight, the halogenating agent preferably being carbon tetrachloride or chloroform in the preferred case when the halogen is chlorine, can advantageously result in rapid and uniform halogenation, preferably chlorination. The use of a support with a smallest average dimension of more than 2 mm would not produce rapid and total halogenation of the support; since the halogen content (% by weight) in the support remains below 4.5% even after a very long halogenation period, maximum activity and selectivity for this type of catalyst is not produced.

In the process for the preparation of the catalyst of the invention, it is also possible to carry out the halogenation treatment prior to the activation and hydrogen reduction step. In this case, reduction in hydrogen can take place remote from the unit (ex situ), requiring particular precautions to be taken to transport the catalyst to the unit. Alternatively, the treatment can be carried out in the unit (in situ) just before using the catalyst.

The catalyst of the invention is used in a conventional isomerisation process for a feed comprising mainly normal paraffins containing 4 to 6 carbon atoms per molecule, preferably 5 to 6 carbon atoms per molecule. The normal operating conditions are indicated below.

Isomerisation takes place in at least one reactor. The temperature is in the range 100° C. to 300° C., preferably in the range 120° C. to 280° C., and the partial pressure of hydrogen is between atmospheric pressure and 7 MPa, preferably in the range 0.5 MPa to 5 MPa. The space velocity is in the range 0.2 liters to 10 liters, preferably in the range 0.5 liters to 5 liters, of liquid hydrocarbons per liter of catalyst per hour. The hydrogen/feed molar ratio at the inlet to the reactor is such that the hydrogen/feed molar ratio in the effluent leaving the reactor is greater than 0.06, preferably in the range 0.06 to 10.

The following examples illustrate the invention without limiting its scope.

EXAMPLE 1

Catalyst A (In Accordance with the Invention)

Gamma alumina was formed by extrusion through a 1.2 mm diameter die. After calcining in air, 0.3% of platinum was deposited on the formed alumina by ion exchange with hexachloroplatinic acid in the presence of HCl as a competing agent. The prepared solid was calcined in air then reduced in hydrogen at 600° C.

The solid was then chlorinated at a temperature of 250° C., by injecting carbon tetrachloride.

EXAMPLE 2

Catalyst B (Not in Accordance with the Invention)

Gamma alumina was formed by extrusion through a 1.2 mm diameter die. After calcining in air, 0.3% of platinum was deposited on the formed alumina by ion exchange with hexachloroplatinic acid in the presence of HCl as a competing agent. The prepared solid was calcined in air then reduced in hydrogen at 600° C.

The solid was then chlorinated at a temperature of 250° C., by injecting hydrogen chloride.

The use of hydrogen chloride rendered the prepared catalyst beyond the scope of the invention.

EXAMPLE 3

Catalyst C (Not in Accordance with the Invention)

Gamma alumina was formed by extrusion through a 2.4 mm diameter die. After calcining in air, 0.3% of platinum was deposited on the formed alumina by ion exchange with hexachloroplatinic acid in the presence of HCl as a competing agent. The prepared solid was calcined in air then reduced in hydrogen at 600° C.

The solid was then chlorinated at a temperature of 250° C., by injecting carbon tetrachloride.

The use of a 2.4 mm die rendered the prepared catalyst beyond the scope of the invention.

EXAMPLE 4

Catalyst D (Not in Accordance with the Invention)

Gamma alumina was formed by extrusion through a 2.4 mm diameter die. After calcining in air, 0.3% of platinum was deposited on the formed alumina by ion exchange with hexachloroplatinic acid in the presence of HCl as a competing agent. The prepared solid was calcined in air then reduced in hydrogen at 600° C.

The solid was then chlorinated at a temperature of 250° C., by injecting hydrogen chloride.

The use of a 2.4 mm die and hydrogen chloride as a chlorinating agent rendered the prepared catalyst beyond the scope of the invention.

EXAMPLE 5

Catalyst E (In Accordance with the Invention)

Gamma alumina was formed by extrusion through a 1.2 mm diameter die. After calcining in air, 0.3% of platinum was deposited on the formed alumina by ion exchange with hexachloroplatinic acid in the presence of HCl as a competing agent. The prepared solid was calcined in air then reduced in hydrogen at 600° C.

The solid was then chlorinated at a temperature of 250° C., by injecting chloroform.

EXAMPLE 6

Catalyst F (In Accordance with the Invention)

A mixture of 90% by weight of eta alumina and 10% of gamma alumina was formed by extrusion through a 1.2 mm diameter die. After calcining in air, 0.3% of platinum was deposited on the formed alumina by ion exchange with hexachloroplatinic acid in the presence of HCl as a competing agent. The prepared solid was calcined in air then reduced in hydrogen at 600° C.

The solid was then chlorinated at a temperature of 250° C., by injecting carbon tetrachloride.

EXAMPLE 7

Catalyst G (In Accordance with the Invention)

A mixture of 90% by weight of eta alumina and 10% of gamma alumina was formed by extrusion through a 1.2 mm diameter die. After calcining in air, 0.3% of platinum was deposited on the formed alumina by ion exchange with hexachloroplatinic acid in the presence of HCl as a competing agent. The prepared solid was calcined in air then reduced in hydrogen at 600° C.

The solid was then chlorinated at a temperature of 250° C., by injecting chloroform.

EXAMPLE 8

Comparison of Chlorination in Catalysts A, B, C, D, E, F, and G

The chlorine content, as a percentage by weight, was monitored as a function of the chlorination period using X ray fluorescence.

Only catalysts A, E, F and G were in accordance with the invention.

TABLE 1

| Chlorination period | 1 hour | 3 hours | 6 hours | 9 hours |
|---|---|---|---|---|
| Cl content catalyst A | 5.4% | 5.9% | 6.2% | 6.4% |
| Cl content catalyst B | 2.9% | 3.5% | 3.7% | 3.8% |
| Cl content catalyst C | 2.7% | 3.7% | 4.3% | 4.4% |
| Cl content catalyst D | 2.8% | 3.2% | 3.5% | 3.7% |
| Cl content catalyst E | 5.0% | 5.7% | 6.1% | 6.2% |
| Cl content catalyst F | 8.5% | 8.7% | 9.1% | 9.8% |
| Cl content catalyst G | 7.9% | 8.4% | 8.9% | 9.2% |

For the two catalysts which were chlorinated with carbon tetrachloride (A and C), it is clear from Table 1 that catalyst A reached a higher chlorine content than catalyst C, and far more rapidly.

For the two catalysts which were chlorinated with hydrogen chloride (B and D), there was practically no difference between the chlorine contents in catalysts B and D. However, chlorination with HCl produced a maximum chlorine content which was lower than that obtained for chlorination with $CCl_4$.

In the case of chlorination with HCl, the diameter of the extrudates appeared to have little effect on the maximum chlorine content and rate of chlorination. In contrast, in the case of chlorination with $CCl_4$, the diameter of the extrudates had a considerable effect on the maximum chlorine content and rate of chlorination.

Catalysts E and G, chlorinated with chloroform, achieved chlorine contents which were close to those obtained by chlorination with carbon tetrachloride (catalysts A and F).

Catalysts F and G, containing eta alumina and gamma alumina, attained substantially equal chlorine contents.

Finally, the use in Examples 1 to 8 of a support extruded through a 1.2 mm die reduced the chlorination period while keeping a maximum chlorine content in the catalyst (which rapidly attained a minimum of 4.5% by weight of chlorine).

EXAMPLE 9

Isomerisation Test for Normal $C_5$–$C_6$ Paraffins

Catalysts A and C prepared above were each tested by isomerising a feed formed of about 60% of normal $C_5$ paraffins and 40% of normal $C_6$ paraffins, the feed containing 100 ppm of $CCl_4$, expressed as the weight of chlorine, to maintain the chlorine content in the catalyst being used.

The operating conditions were as follows:

| | |
|---|---|
| Temperature | 150° C. |
| Pressure | 2 MPa |
| HSV | 2 $h^{-1}$ |
| $H_2$/HC (in effluent) | 0.07 |

The performances obtained after 24 hours of operation are shown in Table 2.

In ratios $iC_x/(i+n)C_x$, x=5, 6, $iC_x$ represents the quantity of isoparaffins containing x carbon atoms in the effluent, and $(i+n)C_x$ represents the quantity of isoparaffins and normal paraffins containing x carbon atoms in the effluent.

The approximate equilibria of the different isomers are defined as follows:

$$AEQi_x = \frac{iC_x/(i+n)C_x \text{ in effluent}}{iC_x/(i+n)C_x \text{ at equilibrium}}$$

where $i_x$=isoparaffin containing x carbon atoms (x=5 or 6).

TABLE 2

| | Catalyst A (invention) | Catalyst C (comparative) |
|---|---|---|
| Cl content (weight %) | 5.9 | 3.7 |
| $iC_5/(I+n)C_5$ | 0.78 | 0.59 |
| $iC_6/(i+n)C_6$ | 0.89 | 0.73 |
| $AEQi_5$(%) | 94.0 | 71.0 |
| AEQ 2,2-dimethylbutane (%) | 88.0 | 60.0 |
| Cracking (weight %) (secondary reaction) | 2.0 | 1.2 |

Catalyst A, in accordance with the invention and with a chlorine content of over 4.5%, performed better than catalyst C which had a lower chlorine content.

EXAMPLE 10

Catalysts H and I

In order to prepare two catalysts with different extrudates diameters (smallest dimension), gamma alumina was formed by extrusion using either a 1.2 mm or a 2.4 mm die. Each support sample was then calcined, and 0.4% Pt was deposited on the formed alumina by ion exchange with hexachloroplatinic acid in the presence of HCl as a competing agent. The solids prepared were then calcined in air, and reduced in hydrogen at 550° C. Aluminum chloride was sublimated on the solids under a hydrogen flow at 550° C, and thereafter flushed with hydrogen for about 1 hour at 600° C. The chlorination treatment lasted 9 hours. The catalysts obtained are referenced as catalysts H (1.2 mm extrudates) and I (2.4 mm extrudates). The chlorine contents are indicated in table 3.

EXAMPLE 11

Catalysts J, K, L, M

In order to prepare 4 catalysts with different extrudates diameters (smallest dimension), gamma alumina was formed by extrusion using either a 0.8 mm, 1.2 mm, 2.0 mm or a 2.4 mm die.

Each support sample was then calcined, and 0.4% Pt was deposited on the formed alumina by ion exchange with hexachloroplatinic acid in the presence of HCl as a competing agent. The solids prepared were then calcined in air, and reduced in hydrogen at 550° C. Aluminum chloride was sublimated on the solids under a hydrogen flow at 550° C., and thereafter flushed with hydrogen for about 1 hour at 600° C. The solid was then further chlorinated by carbon tetrachloride at a temperature of 250° C. The total chlorination treatment (aluminum chloride+carbon tetrachloride) lasted 9 hours.

The catalysts obtained are referenced as catalysts J (0.8 mm extrudates), K (1.2 mm extrudates), L (2.0 mm extrudates) and M (2.4 mm extrudates). The chlorine contents are indicated in table 3.

EXAMPLE 12

Catalysts N and P (In Accordance with the Invention)

Two catalysts were prepared following the preparation procedure of example 1 of U.S. patent application Ser. No. 08/671,340, except that gamma alumina was formed by extrusion with a 0.8 mm or a 2.0 mm diameter die. Chlorination was effected by carbon tetrachloride during 9 hours. The catalysts obtained are referenced N (0.8 mm extrudates) and P (2.0 mm extrudates). The chlorine contents are indicated in table 3.

EXAMPLE 13

Catalysts R and S (Not in Accordance with the Invention)

Two catalysts were prepared following the preparation procedure of example 2 of U.S. patent application Ser. No. 08/671,340, except that gamma alumina was formed by extrusion with a 0.8 mm or a 2.0 mm diameter die. Chlorination was effected by HCl during 9 hours. The catalysts obtained are referenced R (0.8 mm extrudates) and S (2.0 extrudates). the chlorine contents are indicated in table 3.

EXAMPLE 14

Comparison of Catalysts A, B, C, D of U.S. patent application Ser. No. 08/671,340, and Catalyst H, I, J, K, L, M, N, P, R, S The chlorine contents of the catalysts prepared are compared in table 3 thereafter. It is seen that except for HCl, there is an effect of the extrudates diameter on the chlorine content of the catalyst. In particular, a higher chlorine content is obtained for 1.2 mm extrudates (HCl excluded)

TABLE 3

| Chlorinating agent | Chlorine content (wt %) | | | |
|---|---|---|---|---|
| | 0.8 mm | 1.2 mm | 2.0 mm | 2.4 mm |
| CCl4 | 6.0 (N) | 6.4 (A) | 5.8 (P) | 4.4 (C) |
| AlCl3 | | 5.5 (H) | | 3.8 (I) |
| AlCl3 + CCl4 | 5.1 (J) | 5.8 (K) | 4.9 (L) | 4.4 (M) |
| HCl | 3.6 (R) | 3.8 (B) | 3.7 (S) | 3.7 (D) |

EXAMPLE 15

Comparison of Catalysts A, H, K and M Performances

Performances of catalysts A, K and M have been evaluated by isomerising the same C5/C6 feed (60% of normal C5 paraffins and 40% of C6 normal paraffins) under the same operating conditions as in example 9 of U.S. patent application Ser. No. 08/671,340):

H2/HC (moles in effluent)=0.07

H.S. V (h−1)=2

Pressure (Mpa)=2

Temperature=150° C.

The performances obtained are indicated in Table 4:

TABLE 4

| | Catalyst: | | | |
|---|---|---|---|---|
| | A | B | C | D |
| iC5/(i + n)C5 | 0.78 | 0.7 | 0.76 | 0.60 |
| iC6/(i + n)C6 | 0.89 | 0.78 | 0.84 | 0.73 |

EXAMPLE 16

Catalyst T

Gamma alumina is formed by oil-dropping to obtain spheres of 1.2 mm diameter. The spheres are impregnated by 0.3 wt % of Pt by ionic exchange of hexachloroplatinic acid. Excess solution is evaporated to dryness in a rotary evaporator. The dried and evaporated spheres are subsequently calcined at 550° C. under air flow during 2 hours, and then reduced under hydrogen at 550° C. for 1 hour. Aluminum chloride is then sublimated on the spheres at 550° C. under a hydrogen during 1.5 hours, and the solid thereafter flushed with hydrogen for about 1 hour at 600° C. The solid is then further treated by carbon tetrachloride for 2 hours at 300° C., under a nitrogen flow. The catalyst obtained is then flushed with nitrogen for 1 hour at 300° C. It contains 5.1 wt % of chlorine.

EXAMPLE 17

Catalyst U

Gamma alumina is formed by oil-dropping to obtain spheres of 1.2 mm diameter. The spheres are impregnated by 0.3 wt % of Pt by ionic exchange of hexachloroplatinic acid. Excess solution is evaporated to dryness in a rotary evaporator. The dried and evaporated spheres are subsequently calcined at 550° C. under air flow during 2 hours, and then reduced under hydrogen at 600° C. for 1 hour. The solid are then further treated by carbon tetrachloride for 3.5 hours at 300° C., under a nitrogen flow. The catalyst obtained is then flushed with nitrogen for 1 hour at 300° C. It contains 4.8 wt % of chlorine.

EXAMPLE 18

Comparison of the Performances of Catalysts T and U

Performances of catalysts T and U have been evaluated by isomerising a C5/C6 feed containing 50% of normal C5 paraffins and of C6 normal paraffins, under the following operating conditions:

H2/HC (mole in effluent)=0.125
H.S.V. (h−1)=2
Pressure (Mpa)=0.7
Temperature=140° C.

The results obtained after 500 hours on stream are indicated in Table 5:

TABLE 5

|  | Catalyst: | |
| --- | --- | --- |
|  | T | U |
| Chlorine content (wt %) | 5.1 | 4.8 |
| iC5/(i + n)C5 | 0.68 | 0.72 |
| iC6/(i + n)C6 | 0.7 | 0.74 |

Catalyst U prepared with carbon tetrachloride as the chlorinating agent leads to better results than catalyst T having the same sphere diameter (1.2 mm), but chlorinated with both aluminum chloride and carbon tetrachloride.

EXAMPLE 19

Catalyst V

Gamma alumina spheres of about 1.6 mm diameter were impregnated with 0.4 wt % platinum, by immersing the spheres in an aqueous chloroplatinic acid solution, and evaporating the solution to dryness in contact with the spheres in a rotary evaporator. The dried impregnated spheres were then calcined at 550° C. in an air stream for 2 hours, and then in a stream of hydrogen at the same temperature for 1 hour.

52 grams of aluminum chloride was vaporized and passed in contact with 125 grams of the reduced, platinum-impregnated spheres during 1.5 hours, and at 550° C., using hydrogen as a carrier gas at a flow-rate of 850 cm 3/min. The spheres were then flushed with hydrogen for about 1 hour at 600° C.

60 grams of carbon tetrachloride were then passed in contact with the spheres during 1.5 hours at 300° C., using nitrogen as the carrier gas at a flow-rate of about 2000 cm3/min. The catalyst was then flushed with nitrogen for 1 hour at 300° C. to remove unreacted carbon tetrachloride. The catalyst V obtained contains 6.0 wt % of chloride.

EXAMPLE 20

Catalyst W

Gamma alumina spheres of about 1.6 mm diameter were impregnated with 0.4 wt % platinum, by immersing the spheres in an aqueous chloroplatinic acid solution, and evaporating the solution to dryness in contact with the spheres in a rotary evaporator. The dried impregnated spheres were then calcined at 550° C. in an air stream for 2 hours, and then in a stream of hydrogen at 600° C. for 1 hour.

70 grams of carbon tetrachloride were then passed in contact with 125 grams of the reduced, platinum-impregnated, spheres during 2.5 hours at 300° C., using nitrogen as the carrier gas at a flow-rate of about 2000 cm3/min. The catalyst was then flushed with nitrogen for 1 hour at 300° C. to remove unreacted carbon tetrachloride. The catalyst W obtained contains 6.0 wt % of chloride.

EXAMPLE 21

Comparison of Catalysts V and W Performances

Performances of catalysts V and W have been evaluated on the same C5/C6 feed and under the same operating conditions as in Example 18.

The results obtained after 24 hours on stream are indicated in Table 6.

TABLE 6

|  | Catalyst: | |
| --- | --- | --- |
|  | V | W |
| Chlorine content (wt %) | 6.0 | 6.0 |
| iC5/(i + n)C5 | 0.70 | 0.75 |
| iC6/(i + n)C6 | 0.76 | 0.83 |

Comparing the present invention to that of Goble et al. (U.S. Pat. No. 3,553,281), in Examples 1 to 7, 9 to 12 and 14 to 16 of Goble et al., a commercial reforming catalyst is used which already contain chlorine (up to 0.81 wt %). This chlorine is not removed before chlorination by carbon tetrachloride or chloroform. Thus, the chlorine contained in the Goble et al. catalysts comes not only from carbon tetrachloride or chloroform. In the present invention, the chlorine coming from the impregnation of Group VIII metals is removed by calcination and a preferred reduction under hydrogen (illustrated in the Examples).

In Example 9, PdCl2 and HCl also act as potential chlorinating agents, and are not fully removed by calcination at 450° C. before chlorination by carbon tetrachloride. In Example 13, no Group VIII metal is involved.

The preceding examples of the present invention can be repeated with similar success by substituting the generically or specifically described reactants and/or operating conditions of this invention for those used in the preceding examples.

The entire disclosure of all applications, patents and publications, cited above and below, and of corresponding French application 95/07.887, are hereby incorporated by reference.

From the foregoing description, one skilled in the art can easily ascertain the essential characteristics of this invention, and without departing from the spirit and scope thereof can make various changes and modifications of the invention to adapt it to various usages and conditions.

We claim:

1. A catalyst containing chlorine, platinum and a formed support comprising gamma alumina and optionally eta alumina, the catalyst being characterized in that the smallest average dimension of said support is in the range 0.8 mm to 2 mm, that the chlorine content is in the range of 4.5% to 15% by weight, said catalyst having been prepared by immersing gamma alumina spheres or extrudates in an aqueous chloroplatinic acid solution, evaporating the solution to dryness, calcining the resultant dried impregnated spheres or extrudates in an air stream to remove chlorine, contacting the resultant platinum impregnated spheres or extrudates with carbon tetrachloride as the only halogenating agent, and removing unreacted carbon tetrachloride.

2. A catalyst according to claim 1, in which the support is essentially formed of extrudates.

3. A catalyst according to claim 1, in which the support is essentially formed of spheres.

4. A catalyst according to claim 1, in which the gamma alumina has a specific surface area in the range 150 $m^2/g$ to 300 $m^2/g$ and a pore volume in the range 0.4 $cm^3/g$ to 0.8 $cm^3/g$ and in which the eta alumina, if present in the support of said catalyst, has a specific surface area in the range 400 $m^2/g$ to 600 $m^2/g$ and a pore volume in the range 0.3 $cm^3/g$ to 0.5 $cm^3/g$.

5. A catalyst according to claim 1, optionally containing eta alumina and wherein the gamma alumina has a specific surface area in the range of 150 $m^2/g$ to 300 $m^2/g$ and a pore volume in the range of 0.4 $cm^3/g$, the eta alumina, if present in the support of said catalyst, has a specific surface area in the range of 400 $m^2/g$ to 600 $m^2/g$ and a pore volume in the range of 0.3 $cm^3/g$.

6. A catalyst according to claim 5, wherein the contacting of the resultant platinum impregnated spheres or extrudates with carbon tetrachloride was conducted offsite.

7. A catalyst according to claim 1, wherein the chlorine content is 5–12% by weight.

8. A catalyst according to claim 1, wherein following the calcination of the dried impregnated spheres or extrudes in an air stream, the resultant calcined spheres or extrudates are further treated in a stream of hydrogen prior to contacting the resultant reduced spheres or extrudates with carbon tetrachloride.

9. A catalyst according to claim 1, wherein any chlorine in the catalyst is removed prior to contacting the resultant platinum impregnated spheres with carbon tetrachloride.

10. A catalyst according to claim 9, wherein following the calcination of the dried impregnated spheres or extrudates in an air stream, the resultant reduced spheres or extrudates are further treated in a stream of hydrogen prior to contacting the resultant reduced spheres or extrudates with carbon tetrachloride.

11. A catalyst according to claim 1, in which the support also comprises said eta alumina.

12. A catalyst according to claim 1, wherein the contacting of the resultant platinum impregnated spheres or extrudates with carbon tetrachloride was conducted offsite.

* * * * *